(12) United States Patent
Ziegler

(10) Patent No.: US 7,417,151 B2
(45) Date of Patent: Aug. 26, 2008

(54) BORON-BASED ORGANIC CATIONS AND RELATED METHODS

(75) Inventor: Christopher J. Ziegler, Akron, OH (US)

(73) Assignee: The University of Akron, Akron, OH (US)

( * ) Notice: Subject to any disclaimer, the term of this patent is extended or adjusted under 35 U.S.C. 154(b) by 563 days.

(21) Appl. No.: 11/010,222

(22) Filed: Dec. 10, 2004

(65) Prior Publication Data

US 2006/0124902 A1 Jun. 15, 2006

(51) Int. Cl.
*C07D 249/04* (2006.01)
*C07D 403/00* (2006.01)
*C07D 233/00* (2006.01)
*C07D 231/10* (2006.01)

(52) U.S. Cl. .................. 548/255; 548/262.2; 548/300.1; 548/373.1

(58) Field of Classification Search ................. 514/359, 514/383, 385, 403; 548/255, 262, 2, 300.1, 548/373.1
See application file for complete search history.

(56) References Cited

U.S. PATENT DOCUMENTS 5,221,761 A 6/1993 Jen et al.

5,817,724 A 10/1998 Aoki et al.

FOREIGN PATENT DOCUMENTS

EP 0 617 052 A2 9/1994
EP 0 816 386 A2 1/1998

OTHER PUBLICATIONS

Lopez et al. (J. Organometallic Chemistry, vol. 502, 1995, pp. 265-276).*
Trofimenko (J.A.C.S., vol. 89(13), Jun. 21, 1967, pp. 3170-3177).*
Trofimenko (JACS, 89(13), 1967, pp. 3170-3177).*
"The Structure of Hydrotris(imidazolyl)boratothallium(I)—the First Structurally Authenti-..." by Christoph Janiak et al., Z. Anorg. Allg. Chem. 2000, 626, p. 1265-1267.
"Separation of Transition Metals with Poly(pyrazolyl)borates by Solvent Extrac-..." by Tsuyoshi Kitano et al., Analytical Sciences 2001, vol. 17 Supplement, p. i1113-i1116.

* cited by examiner

*Primary Examiner*—Rei-Tsang Shiao
*Assistant Examiner*—Susannah Chung
(74) *Attorney, Agent, or Firm*—Roetzel & Andress; George W. Moxon, II

(57) ABSTRACT

Generally disclosed are boron-based organic cations, a method for their manufacture, a method for their use in ionic liquids, and a method for their use as phase-transfer catalysts. More specifically, the boron-based organic cations have an charge of 1+, 2+, or 3+.

16 Claims, 2 Drawing Sheets

BORON-BASED ORGANIC CATIONS AND RELATED METHODS

TECHNICAL FIELD

This invention relates to boron-based organic cations and related methods. More specifically, the methods are directed to: a method for manufacturing boron-based organic cations, a method for using boron-based organic cations in ionic liquids, and a method for using boron-based organic cations as phase-transfer catalysts.

BACKGROUND OF THE INVENTION

Phase-transfer catalysis (PTC) is known. As the chemical industry has sought to improve its processing efficiency, eliminate safety risks, and reduce its detrimental impact on the environment, PTC has become a recognized tool.

Conventional PTC methodology involves two immiscible phases—typically an aqueous polar phase and an organic nonpolar phase, a phase-transfer catalyst that is soluble in each phase, a substrate that is soluble in the nonpolar phase, and an anionic reagent that is soluble in the polar phase. The phase-transfer catalyst increases the reaction rate between the substrate and anionic reagent by shuttling back and forth between the two phases. The shuttling thereby transports anionic reagents into the organic phase—where reaction with the substrate can occur.

Quaternary ammonium and phosponium salts, with their unique capability to dissolve in both polar and nonpolar phases, are the catalysts of choice for most phase-transfer applications. Ammonium derivatives are the most commonly used, but phosphonium-based phase-transfer catalysts are also commonly used due to their relatively high thermal stability. Other phase-transfer catalysts include crown ethers and polyethylene glycols (PEG).

Some examples of well-known reactions that can be performed by PTC include: nucleophilic substitution reactions, e.g., halogenations and cyanations; alkylation and condensation reactions; oxidations and reductions; elimination reactions; and Wittig and Wittig-Horner reactions.

There are several advantages to using PTC over other reaction systems that employ only a single phase, and those advantages can include: increased reaction rates, lower reaction temperatures, and decreased production costs because costly anhydrous or aprotic solvents are not employed. Additionally, some reactions are known to occur via PTC that would not otherwise occur in a single-phase reaction system.

The overall efficiency of PTC can be influenced by a number of factors such as the steric hindrance associated with the phase-transfer catalyst, the phase-transfer catalyst's lipophilicity, and the lipophilicity of its counter ion.

Ionic liquids are known and generally understood to be made up of anions and cations. When organic cations are generated with moderately long alkyl chains and combined with haloaluminate or halophosphate counter ions, compounds result that have relatively low melting points. Organic salts that have low melting points can be used as solvents for organic reactions, and they have recently received much attention as ionic liquids in both industrial and academic settings. For example, carrying out chemical reactions in ionic liquids is of interest in the growing field of green chemistry, because ionic liquids have negligible vapor pressure. In addition, ionic liquids have also been employed in biphasic catalysis with water to immobilize a homogeneous catalyst in an organic phase. The chemistry of ionic liquids has been reviewed extensively.

There is therefore a need for additional phase-transfer catalysts and additional ionic liquids because of the commercial demand for both.

SUMMARY OF THE INVENTION

In general, the present invention provides a cation having the formula:

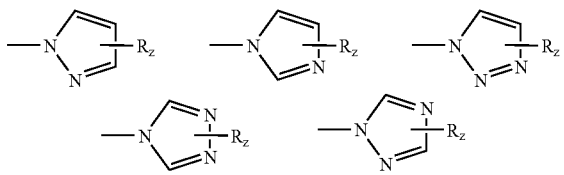

wherein n is an integer that is greater than or equal to 1;
wherein each A is a diazole or triazole that is independently selected from the group consisting of:

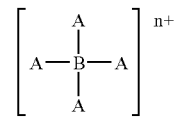

wherein each R is bonded to at least one carbon atom or at least one nitrogen atom;
wherein when an R is bonded to at least one carbon atom, each R is independently selected from the group consisting of a hydrogen atom, a nitrogen-containing heterocycle, a diazole heterocycle, a triazole heterocycle, an alkyl moiety, and a nitrogen-containing alkyl moiety;
wherein when an R is bonded to at least one nitrogen atom, each R is independently selected from the group consisting of a hydrogen atom and an alkyl moiety;
wherein at least two of the cation's exterior nitrogen atoms have alkyl moieties bonded thereto; and
wherein each z is independently selected and is an integer greater than or equal to 0.

The present invention also includes a method for manufacturing a cation comprising the step of:
attaching two or more alkyl moieties to two or more external nitrogens of a compound having the formula:

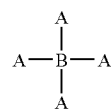

wherein each A is a diazole or triazole selected from the group consisting of:

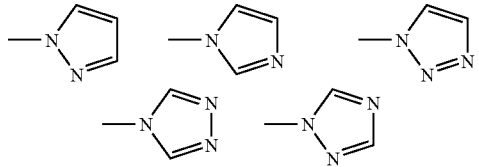

This invention advantageously provides cations having a highly polar character and likewise a high degree of charge in the tris and tetrakis embodiments of the alkylated compounds.

DETAILED DESCRIPTION OF ILLUSTRATIVE EMBODIMENTS

Figure 1:
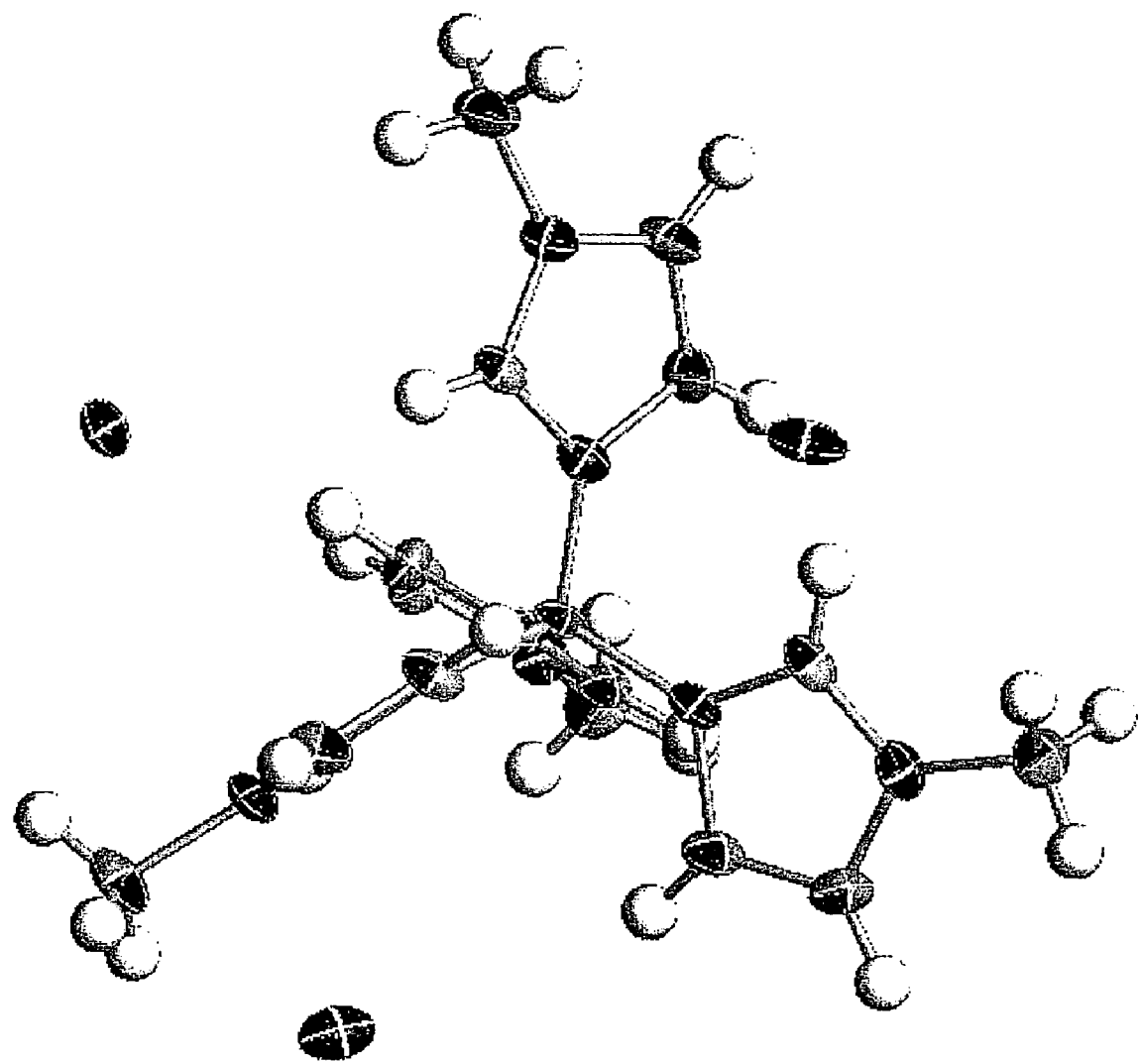
FIG. 1 is a structure from single crystal x-ray diffraction of [B(MeIm)$_4$]I$_3$.
Figure 2:
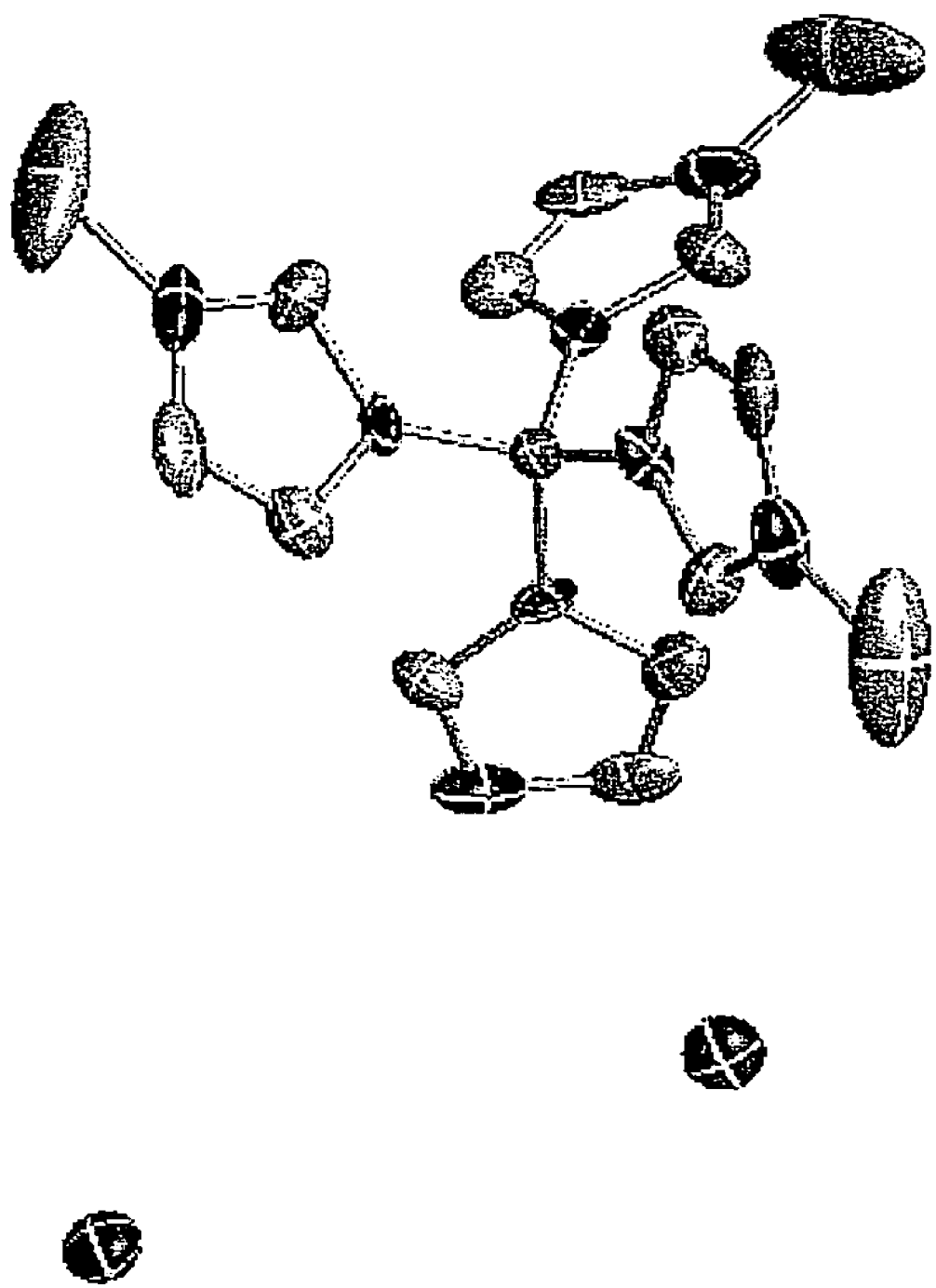
FIG. 2 is a structure from single crystal x-ray diffraction of [B(MeIm)$_3$(Im)]I$_2$. Hydrogen atoms have been omitted for clarity.

This invention is generally directed to boron-based organic cations, a method for making the same, and methods for using these cations in ionic liquids or as phase-transfer catalysts.

The cations can generally be described by the following chemical formula:

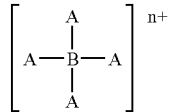

wherein n is an integer that is greater than or equal to 1;

wherein each A is a diazole or triazole that is independently selected from the group consisting of:

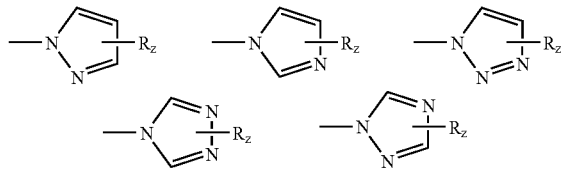

wherein each R is bonded to at least one carbon atom or at least one nitrogen atom;

wherein when an R is bonded to at least one carbon atom, each R is independently selected from the group consisting of a hydrogen atom, a nitrogen-containing heterocycle, a diazole heterocycle, a triazole heterocycle, an alkyl moiety, and a nitrogen-containing alkyl moiety;

wherein when an R is bonded to at least one nitrogen atom, each R is independently selected from the group consisting of a hydrogen atom and an alkyl moiety;

wherein at least two of the cation's exterior nitrogen atoms have alkyl moieties bonded thereto; and wherein each z is independently selected and is an integer greater than or equal to 0.

Nonlimiting specific examples of this invention's organic cations are represented by the following two chemical drawings:

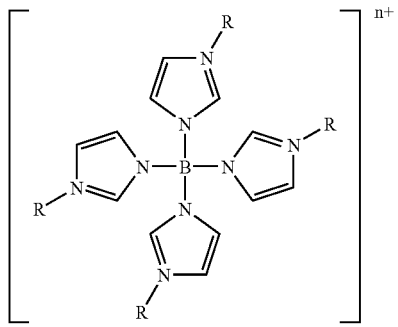

and

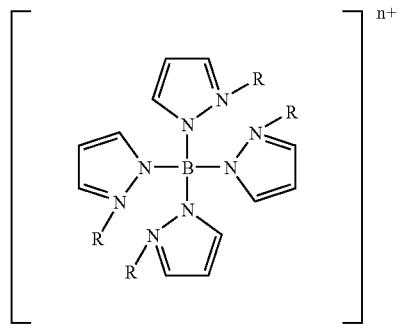

wherein each R is independently selected and is either an alkyl functional group or hydrogen atom;

wherein at least two of the R variables are alkyl functional groups; and wherein n is an integer that is 1, 2, or 3.

The possible charges of this invention's cations are 1+, 2+, and 3+. The charge of this invention's cations can be calculated as a function of the total number of alkyl functional groups on the cation's exterior nitrogens. Where there are exactly two alkyl functional groups on a cation's exterior nitrogens, the charge is 1+; where there are exactly three alkyl functional groups on a cation's exterior nitrogens, the charge is 2+; and where there are exactly four alkyl functional groups on a cation's exterior nitrogens, the charge is 3+. In other words, the value of the charge is equal to one less than the total number of alkyl functional groups on the cation's exterior nitrogens. Preferably, where two or more alkyl groups are on a cation's exterior nitrogen atoms, each exterior nitrogen atom has only one alkyl functional group thereon.

An exterior nitrogen atom is a nitrogen heteroatom of a diazole or triazole that isn't directly bonded to the cation's central boron atom.

There are no limitations on the types of alkyl functional groups that are employable with this invention's cations. Nonlimiting examples of useful alkyl functional groups are: methyl, ethyl, propyl, isopropyl, butyl, t-butyl, sec-butyl, pentyl, isopentyl, octyl, nonyl, decyl, undecyl, dodecyl, cycloalkanes, hydroxylakyl, benzylalkyl, phenylalkyl, heterocyclicalkyl, arylalkyl, fluoroalkyl, choroalkyl, alkoxylalkyl, vinylalkyl, alkenylalkyl, aminoalkyl, alkylamides, alkylacetates, alkylesters, alkylaldehydes, alkylketones, alkylthioethers, and alkylthiolates.

In one embodiment, the boron-based organic cations are manufactured by alkylating either tetrakis(imidazolyl)borate or tetrakis(pyrazolyl)borate. As mentioned above, the degree of alkylation of each of the above-mentioned compounds affects the compound's overall charge by creating a cationic character such that the charge is equal to one less than the total number of alkyl functional groups on the exterior nitrogen atoms. More generally, as the degree of nitrogen-heteroatom alkylation increases, so does the compound's charge.

Tetrakis(pyrazolyl)borate is represented as follows:

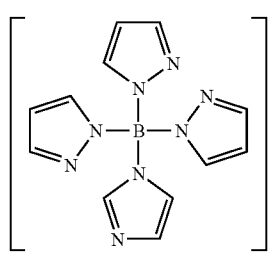

Tetrakis(imidazolyl)borate is represented as follows:

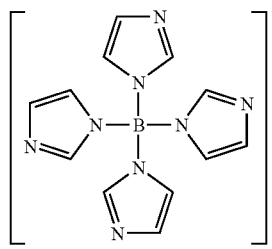

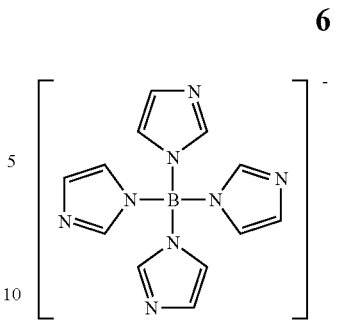

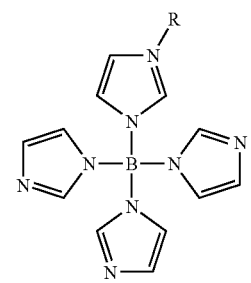

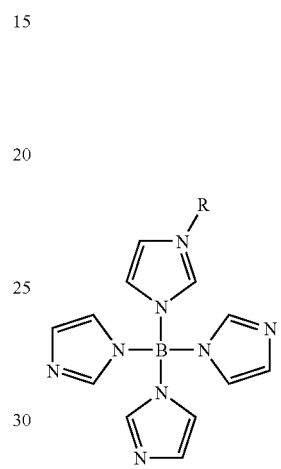

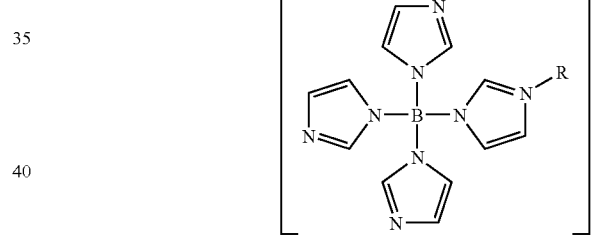

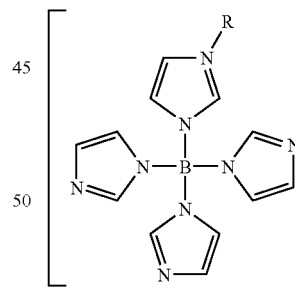

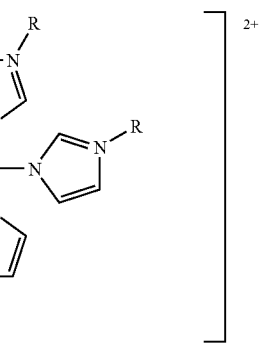

The step of alkylating tetrakis(pyrazolyl)borate or tetrakis (imidazolyl)borate can be performed by any conventional method. In one embodiment for alkylating the subject compounds, an alkylating agent is employed. Generally, an alkylating agent is a compound comprising an alkyl moiety and a halogen functional group; the alkylating agent being represented as R—X. The alkyl functional group (R) is as defined above. The halogen functional group (X) can be any halogen, but iodine is preferred. Nonlimiting examples of preferred alkylating agents are: alkyliodides, alkylbromides, organic sulfonamaides, organic sulfates, alkyloxonium ions, and aldehydes.

Alkylating agents are preferably employed with tetrakis (pyrazolyl)borate or tetrakis(imidazolyl)borate in a relative mole ratio that is greater than or equal to 2:1. When an charge of 1+ is the goal, the relative mole ratio is about 2:1; when an charge of 2+ is the goal, the relative mole ratio is about 3:1; and when an charge of 3+ is the goal, the relative mole ratio is about 4:1.

When alkylating agents are employed to alkylate the subject compounds, the reaction is not limited to any particular temperature range. Preferred temperatures for alkylating the subject compounds are well known and range from about −40 to about 200° C. More preferably, the temperatures range from about 0 to about 150° C.

In one embodiment, alkylation occurs by the following reaction mechanism:

-continued

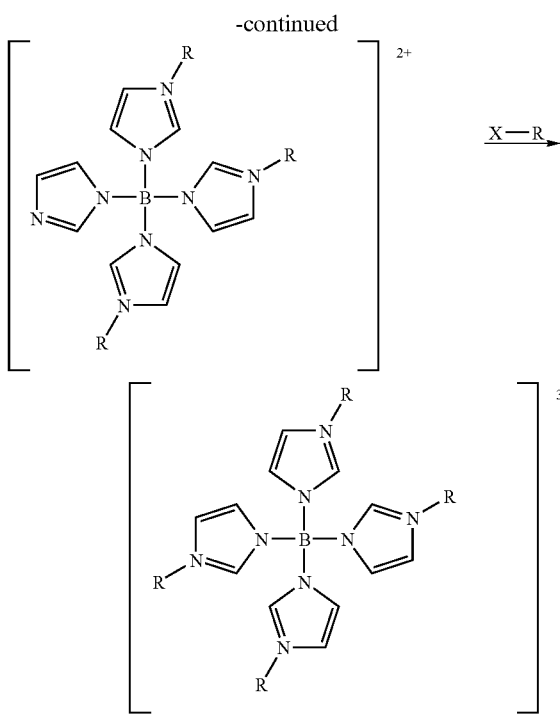

wherein X is a halogen; and wherein R is an alkyl functional group.

The invention's organic cations can be employed as phase-transfer catalysts. In practicing this method, the invention's organic cations are employed at a relative mole ratio to the reactants ranging from about 0.001 to about 100 mole %. Preferably, this invention's organic cations are employed at a relative mole ratio to the reactants ranging from about 0.01 to about 40 mole %. More preferably, the relative mole ratio ranges from about 0.02 to about 20 mole %.

Phase-transfer catalysis is well known and generally requires the use of two immiscible liquid phases. Commonly, one of the liquid phases is polar, and the other is nonpolar. Any nonpolar phase can be employed, and nonlimiting examples of useful nonpolar phases include the following liquids: pentane, petroleum ether, hexane, cyclohexane, heptane, benzene, toluene, xylene, chlorobenzene, dichlorobenzene, chloroform, methylene chloride, and carbon tetrachloride.

Polar liquid phases are also employed, and any polar phase can be used. Nonlimiting examples of employable polar liquids include: methanol, ethanol, tetrahydrofuran, acetone, acetonitrile, pyridine, dimethylformamide and dimethylsulfoxide.

The temperature at which phase-transfer catalysis is conducted is in no way restricted, however, there are preferred temperature ranges. Generally, phase transfer catalysis is performed at a temperature ranging from about 0 to about 200° C. More preferably, the temperature ranges from about 25 to about 125° C.

This invention's organic cations are also employable in ionic liquids. Specifically, this invention's organic cations are used in combination with anionic counterions.

Nonlimiting examples of counteranions that can be employed with this invention's organic cations in manufacturing an ionic liquid are among the following: fluoride, chloride, bromide, iodide, perchlorate, nitrate, sulfate, hexafluorophosphate, acetate, cyanide, thiocyanide and cyanate.

The concentration of this invention's organic cations in an ionic liquid can vary depending on the charge of the cation. When the charge of the organic cation of this invention is 3+, its concentration in the ionic liquid ranges from about 0.001 to about 30 mole %. Preferably, when its charge is 3+, its concentration in the ionic liquid ranges from about 0.01 to about 10 mole %.

When this invention's organic cations have an charge of 2+, these cations are employed in an ionic liquid at a concentration ranging from about 0.001 to about 60 mole %. Preferably, when the charge of this invention's organic cations is 2+, their concentration in the ionic liquid ranges from about 0.02 to about 20 mole %.

When this invention's organic cations have an charge of 1+, their concentration in an ionic liquid ranges from about 0.001 to about 100 mole %. Preferably, when this invention's organic cations have an charge of 1+, their concentration in the ionic liquid ranges from about 0.03 to about 30 mole %.

EXAMPLES

In order to demonstrate the present invention, the following examples have been prepared and tested. The examples should not, however, be viewed as limiting the scope of the invention. The claims will serve to define the invention.

At least the following molecules have been prepared: tetrakis(N-methylimidazole)boron triiodide, (N-methylimidazole)boron tris(hexafluorophosphate), (imidazole)tris(N-methylimidazole) boron diiodide, (imidazole)tris(N-methylimidazole) boron bis(hexafluorophosphate), bis(imidazole)bis(N-methylimidazole)boron iodide, bis(imidazole)bis(N-methylimidazole)boron hexafluorophosphate, tetrakis(N-methyl-pyrazole)boron triiodide, and tetrakis(N-methylpyrazole)boron tris(hexafluorophosphate).

$[B(N-MeAz)_4]I_3$ where Az=imidazole, pyrazole: eight equivalents of $CH_3I$ (8 mmol, 1.14 g) was added to a solution of 1 mmol of $NaB(Az_4)$ in 30 mL of ethanol. The resultant solution was allowed to stir overnight, affording a white precipitate that was collected by filtration. Recrystallization of this white product from water resulted in yields of 50-80% of $[B(N-MeAz)_4]I_3$.

$[B(N-MeAz)_n(Az)_{4-n}]I_{n-1}$ where n=1, 2 or 3: a stoichiometric amount of $CH_3I$ (n mmol) was added to solutions of 1 mmol of $NaB(Az_4)$ in 30 mL of ethanol. The resultant solutions were allowed to stir overnight, affording a white precipitate that was collected by filtration. Recrystallization of the products were carried out in water. Yields ranged from 22-50% for these reactions.

Anion exchange of cationic borates: The iodide in the above compounds could be exchanged for hexafluorophosphate by precipitation from a saturated solution of $NH_4PF_6$ in water. Yields were quantitative.

In light of the foregoing, it should thus be evident that the present invention substantially improves the art. While, in accordance with the patent statutes, only the preferred embodiments of the present invention have been described in detail hereinabove, the present invention is not to be limited thereto or thereby. Rather, the scope of the invention shall include all modifications and variations that fall within the scope of the attached claims.

What is claimed is:

1. A cation having the formula:

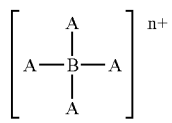

wherein n is an integer that is greater than or equal to 1;
wherein each A is a diazole or triazole that is independently selected from the group consisting of:

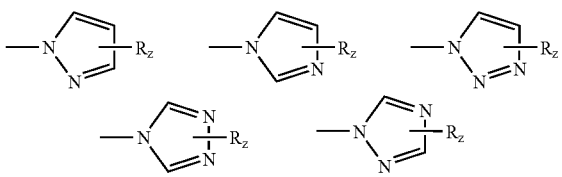

wherein each R is bonded to at least one nitrogen atom and may also be bonded to one or more carbon atoms.
wherein when an R is bonded to one or more carbon atom, each R is independently selected from the group consisting of a hydrogen atom, a nitrogen-containing heterocycle, a diazole heterocycle, a triazole heterocycle, an alkyl moiety, and a nitrogen-containing alkyl moiety;
wherein when an R is bonded to at least one nitrogen atom, each R is independently selected from the group consisting of a hydrogen atom and an alkyl moiety;
wherein at least two of the cation's exterior nitrogen atoms have alkyl moieties bonded thereto; and
wherein each z is independently selected and is an integer greater than or equal to 0.

2. The cation of claim 1, wherein the alkyl moiety is a $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$ alkyl moiety.

3. The cation of claim 1, wherein the alkyl moiety is a methyl, ethyl, propyl, isopropyl, butyl, t-butyl, sec-butyl, pentyl, isopentyl, octyl, nonyl, decyl, undecyl, dodecyl, cycloalkanes, hydroxylakyl, benzylalkyl, phenylalkyl, heterocyclicalkyl, arylalkyl, fluoroalkyl, choroalkyl, alkoxylalkyl, vinylalkyl, alkenylalkyl, aminoalkyl, alkylamides, alkylacetates, alkylesters, alkylaldehydes, alkylketones, alkylthioethers, or alkyithiolates.

4. The cation of claim 1, wherein exactly two of the cation's exterior nitrogen atoms have alkyl moieties bonded thereto.

5. The cation of claim 1, wherein exactly three of the cation's exterior nitrogen atoms have alkyl moieties bonded thereto.

6. The cation of claim 1, wherein exactly four of the cation's exterior nitrogen atoms have alkyl moieties bonded thereto.

7. The cation of claim 1, wherein five or more of the cation's exterior nitrogen atoms have alkyl moieties bonded thereto.

8. The cation of claim 1, wherein z is 3 or 4.

9. A method for performing phase-transfer catalysis comprising the steps of:
providing two immiscible liquid phases and a substrate and a reagent as reactants; and employing the cation of claim 1 at a relative mole ratio to the reactants of from 0.001 to 100 mole % as phase-transfer catalyst.

10. An ionic liquid comprising the cation of claim 1.

11. A method for manufacturing a cation comprising the step of:
providing a compound having the formula:

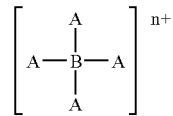

wherein each A is a diazole or triazole selected from the group consisting of:

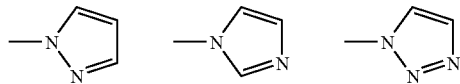

and attaching two or more alkyl moieties to two or more external nitrogens by employing an alkylating agent selected from the group consisting of alkyliodides, alkylbromides, organic sulfonamides, organic sylfates, alkyloxonium ions, and aldehydes at a relative mole ratio of at least 2:1.

12. The method of claim 11, wherein the two or more alkyl moieties are selected from the group consisting of a $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$ alkyl moiety, and combinations thereof.

13. The method of claim 11, wherein exactly two alkyl moieties are attached to the cation's exterior nitrogens.

14. The method of claim 11, wherein exactly three alkyl moieties are attached to the cation's exterior nitrogens.

15. The method of claim 11, wherein exactly four alkyl moieties are attached to the cation's exterior nitrogens.

16. The method of claim 11, wherein five or more alkyl moieties are attached to the cation's exterior nitrogens.

* * * * *